United States Patent [19]

Tinker et al.

[11] Patent Number: 5,492,111
[45] Date of Patent: Feb. 20, 1996

[54] METHOD OF ELIMINATION OF VOLATILE DEGRADATION PRODUCTS OF SEVOFLURANE DURING ANESTHESIA

[75] Inventors: John H. Tinker; Max T. Baker, both of Iowa City, Iowa

[73] Assignee: University of Iowa Research Foundation, Oakdale, Iowa

[21] Appl. No.: 79,165

[22] Filed: Aug. 12, 1993

Related U.S. Application Data

[63] Continuation-in-part of Ser. No. 10,264, Jan. 28, 1993, abandoned.

[51] Int. Cl.$^6$ .................................................. A61M 15/00
[52] U.S. Cl. ................................ 128/203.12; 128/205.12; 128/204.15; 128/204.16
[58] Field of Search .......................... 128/203.12, 204.15, 128/204.16, 205.12

[56] References Cited

U.S. PATENT DOCUMENTS

| | | | |
|---|---|---|---|
| 999,451 | 8/1911 | Holleman | 128/204.16 |
| 1,858,400 | 5/1932 | Koehler | 128/204.15 |
| 2,099,954 | 11/1937 | Cook | 128/204.16 |
| 2,571,014 | 10/1951 | Colburn et al. | 128/204.16 |
| 2,980,112 | 4/1961 | Snyder | 128/204.16 |
| 3,346,448 | 10/1967 | Gilbert | 514/722 |
| 3,476,860 | 11/1969 | Croix et al. | 514/722 |
| 3,592,191 | 7/1971 | Jackson | 128/204.16 |
| 3,683,092 | 8/1972 | Regan et al. | 514/723 |
| 3,714,942 | 2/1973 | Fischel et al. | 128/204.16 |
| 3,883,665 | 5/1975 | Croix | 514/722 |
| 4,069,346 | 1/1978 | McCarty | 514/743 |
| 4,142,525 | 5/1979 | McCarty | 604/121 |
| 4,154,971 | 5/1979 | Larsen et al. | 514/816 |
| 4,188,405 | 2/1980 | Larsen et al. | 514/722 |
| 4,250,334 | 2/1981 | Coon et al. | 568/683 |
| 4,328,376 | 5/1982 | Berger et al. | 568/682 |
| 4,874,902 | 10/1989 | Huang et al. | 568/683 |
| 4,996,371 | 2/1991 | Halpern et al. | 568/683 |
| 5,044,361 | 9/1991 | Werner et al. | 128/204.16 |

FOREIGN PATENT DOCUMENTS 1170702  11/1969  United Kingdom .

OTHER PUBLICATIONS

Morio et al., Anesthesiology 77:1155–1164, 1992.
Mazze, Anesthesiology, 77:1062–1063, 1992.
Frink, et al., Anesthesiology, 77:1064–1069, 1992.

Primary Examiner—Aaron J. Lewis
Attorney, Agent, or Firm—Charles F. Lind

[57] ABSTRACT

In the process of using sevoflurane as a rapid anesthetic, breakdown of the anesthetic to harmful compound A is slowed if not stopped altogether by cooling the $CO_2$ scrubber to temperatures that still allow it to work effectively as scrubber but avoid sevoflurane degradation.

6 Claims, 2 Drawing Sheets

METHOD OF ELIMINATION OF VOLATILE DEGRADATION PRODUCTS OF SEVOFLURANE DURING ANESTHESIA

CROSS-REFERENCED TO A RELATED APPLICATION

This application is a continuation-in-part of application Baker et al, Ser. No. 08/010,264, filed Jan. 28, 1993, a commonly assigned application, now abandoned.

BACKGROUND OF THE INVENTION

Halogenated isopropyl derivatives of ether have demonstrated promise for use in the medical field due to their anesthesia inducing properties. Of these, the most successful to date has been with fluorinated isopropyl ethers such as sevoflurane (fluoromethyl 1,1,1,3,3,3-hexafluro-2-propyl ether). Sevoflurane has demonstrated rapid induction and recovery from anesthesia when administered by inhalation, making it attractive for use as an anesthetic. Further, sevoflurane is a volatile liquid, nonflammable in air at ambient temperatures and has a lower flammability limit in oxygen of about 11.8 volume percent, making it safe to use as well. U.S. Pat. No. 3,683,092 to Regan et al. discloses use of sevoflurane as an anesthetic.

While exhibiting many beneficial anesthetic properties such as the ability to rapidly change depth of anesthesia, use of sevoflurane as a general inhalational anesthetic has been hampered by its potential nephro-toxicity when metabolized at sufficiently high levels. It is however commonly used in Japan.

Attempts to find other halogenated isopropyl derivatives with beneficial anesthetic properties have led scientists to substitute sevoflurane with other similar moieties. These attempts have not been successful in that several related compounds either do not possess any anesthetic properties, produce only small anesthetic properties, or are toxic. For example, U.S. Pat. No. 3,683,092 discloses that the compound $CH_3OCF(CF_3)_2$ was found to be non-anesthetic up to 8% by volume in oxygen meaning that it would burn at its anesthetic concentration since its lower flammability limit is about 7–8%. Another isomer, trifluoromethyl-2,2,3,3-tetrafluoropropyl ether of Aldrich and Shepard, Jorg., Volume 29, pages 11–15 (1964) has been shown to cause violent convulsions and death in mice at concentrations as low as 0.5%. Yet another isomer, $CHF_2OCH_2CF_2CF_3$ is non-anesthetic up to its lethal concentration and produces convulsions in mice. Still another comparison, it has been found that the isomeric $(CHF_2)_2CF-O-CHF_2$ is a weak anesthetic in which deep anesthesia is not obtained and abnormal electro-encephalographic and convulsant activity is observed. Thus it can be seen that there has been little success to date, and a need exists for an anesthetic for use in mammals which will possess the advantageous characteristics of sevoflurane while minimizing the concomitant fluoride ion release.

Another problem that exists with sevoflurane, relates to degradation products when used in a typical anesthetic circuit involving $CO_2$ absorbants, see Morio, et al "Reaction of Sevoflurane and its Degradation Products with Sodalime: Toxicity of the By-Products", *ANESTHESIOLOGY* 77:1155–1164, 1992 and Frink et al, "Quantification of the degradation products of sevoflurane in two $CO_2$ absorbants during low-flow anesthesia in surgical patients" *ANESTHESIOLOGY* 77:1064–1069, 1992. Although these degradation products eventually include perhaps up to five different compounds, the initial reaction leads to the most prevalent and potentially harmful compound which is known in the art as "Compound A". It is an unsaturated compound of the formula fluoromethyl-2, 2 diflouro-1-trifluoromethyl vinyl ether represented as follows:

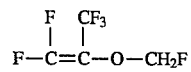

By way of background, a typical anesthetic circuit includes, of course, the anesthetic machine which administers an inhalational anesthetic to the patient, the patient's respiratory system for inhaling of a mixture of oxygen and anesthetic and exhaling anesthetic mixture now having a high carbon dioxide content, a scrubber system to remove carbon dioxide from the exhaled gas mixture then, of course, a recycle system using one-way valves back to the anesthetic circuit. In this semi-closed loop process, the typical carbon dioxide scrubber or absorbant is a canister of a mixture known generally as sodalime. There are perhaps as many as five commercial manufacturers of sodalime for use in anesthesiology. Generally, those mixtures include a mixture of sodium, calcium and potassium hydroxide. Some examples of sodalime commercially available and commonly used in surgery for $CO_2$ absorption or scrubbing are SODASORB™ by W. R. Grace of Lexington, Mass., Barolyme of Chemtron Medical Division, Allied Health Care Products of St. Louis, Mo., and WAKOLIME® (Wako Pure Chemical, Osaka, Japan). Sodalime comprises about 5% sodium hydroxide and about 95% calcium hydroxide. Depending upon the manufacturer, other components present in carbon dioxide scrubber canisters include potassium hydroxide, barium hydroxide, sodium silicate, and of course, water. All are very strong bases.

All of these products operate in generally the same way, that is the sodium hydroxide primarily reacts with carbon dioxide, which produces bicarbonate which in turn reacts with the calcium hydroxide to provide insoluble precipitated carbonates. The reaction is exothermic, and although the canister starts at ambient conditions, by the time the surgery is underway it warms and often reaches a stable temperature within the range of 45° C. to 50° C. The exact steady state temperature reached depends upon the $CO_2$ volume produced by the patient and the total flow of all gases in the air.

As reported in the earlier referenced articles of Morio et al and Frink et al, at elevated temperatures in sodalime, one commonly observes degraded products of sevoflurane which are potentially toxic. In particular there are problems with two different parts of the sevoflurane molecule. The fluoromethoxy carbon portion of the molecule degrades during metabolism in the patient's liver to release fluoride ion which can potentially damage the kidney. The hexafluoroisopropyl portion of the compound, in the presence of sodalime under normal operating conditions, will degrade to provide Compound A, a vinyl unsaturate, which has been demonstrated in the literature to be toxic when inhaled at ranges of from 100 ppm to 1000 ppm during inhalational experiments with rats. Obviously, therefore, although sevoflurane has significant opportunities as an inhalational anesthetic, the organ toxicity issues associated with the use of sevoflurane must first be solved.

In our parent application, Baker et al., Ser. No. 08/010, 264, filed Jan. 29, 1993, and entitled DEUTERATED SEVOFLURANE AS AN INHALATIONAL ANESTHETIC, we discovered that deuterated sevoflurane is metabolized and subsequently defluorinated at a much slower rate than sevoflurane itself, thereby reducing fluoride ion release while still maintaining all of the anesthetic properties of sevoflurane. Although this solves a very important problem with this molecule, namely, liver metabolism to release fluoride ion, it does not solve that portion of the problem that relates to degradation products in the presence of $CO_2$ scrubbers such as sodalime. The present invention represents an improvement on the invention of the parent application and solves the latter sodalime degradation problem. The process may be used with sevoflurane itself or with the deuterated sevoflurane of our parent application.

It is an object of the present invention to provide an improved anesthesia method for use in conjunction with sevoflurane or deuterated sevoflurane as an inhalational anesthetic which will reduce the degradation decomposition of sevoflurane by sodalime scrubbers to the level that release of compound A and other potentially toxic breakdown products of sevoflurane will be trivial and non-toxic.

Yet another object of the present invention is to provide a method for inducing anesthesia in patients involving inhalation of sevoflurane or deuterated sevoflurane but which minimizes or eliminates "Compound A" and/or other degradation products from the anesthetic circuit.

It is yet another object of the present invention to provide a method of inducing anesthesia with sevoflurane which will produce anesthesia in a patient but with a lower organ toxicity risk than normally associated with sevoflurane.

It is a further object of the present invention to provide minimization of degradation products of sevoflurane in a normal anesthetic circuit by controlling the temperature of the carbon dioxide scrubbing canister so that it is at all times at room temperature or lower which, as demonstrated below, minimizes or eliminates the degradation by-products particularly "Compound A".

Further objects of the invention will be demonstrated from the detailed description of the invention which follows.

Summary of the Invention

This invention relates to a process of inducing inhalational anesthesia in mammals, including humans, which employs in a semi-closed anesthetic circuit, a carbon dioxide scrubber which is maintained at all times at ambient temperature or lower. In this manner, the normally exothermic reaction that occurs in the carbon dioxide scrubber is kept cool, and as a result, when the carbon dioxide scrubber or absorbant canister is used with sevoflurane, degradation products are minimized if not eliminated altogether.

DETAILED DESCRIPTION OF THE INVENTION

Figure 1:
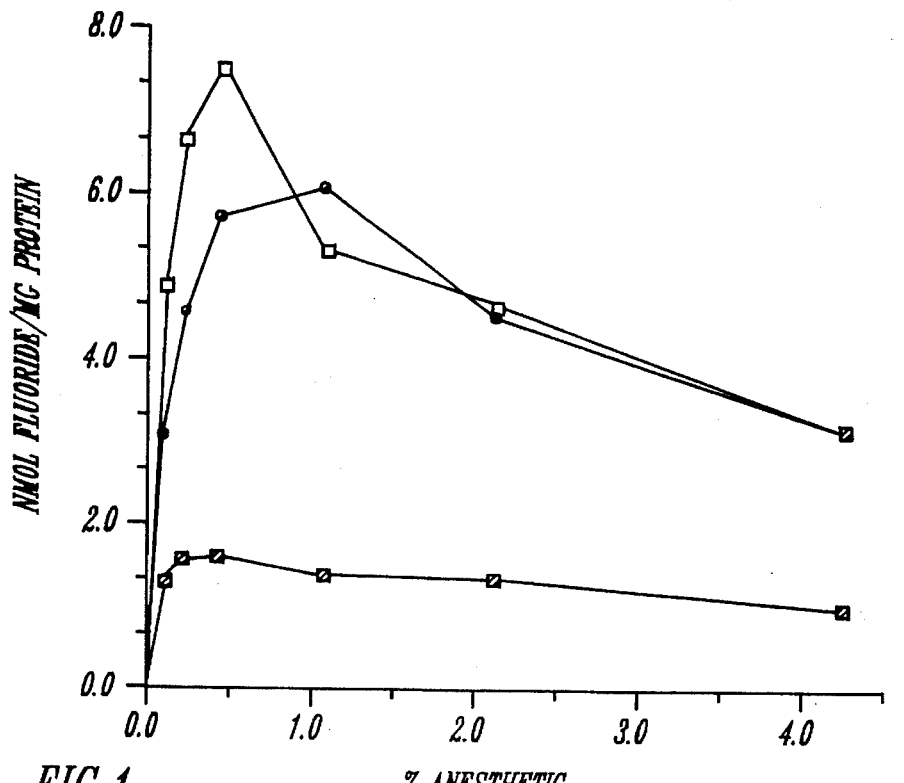
FIG. 1 is a graph depicting concentration dependent defluorination of deuterated sevoflurane, sevoflurane, and enflurane in hepatic microsomes from Isoniazid treated rats.

Sevoflurane, or fluoromethyl 1,1,1,3,3,3 -hexafluoro-2-propyl ether has the following formula:

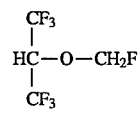

Sevoflurane, upon administration into the body, is metabolized in the liver by cytochrome P450, liberating fluoride and hexafluoroisopropanol. Inorganic fluoride at sufficiently high levels will produce renal dysfunction including polyuric renal failure, which can be fatal.

In addition, as illustrated in the above referenced articles of Morio et al and Frink et al, double bonded breakdown products starting with "Compound A", which are inhaled after formation in sodalime, can irreversibly bind to tissue macromolecules resulting in major organ toxicity. Although the toxicity of these degradation by-products has been mentioned in both the Morio and the Frink articles, nothing is suggested as to how or why those degradation products occur. This invention is premised upon the discovery that those degradation products occur because of the normally high (45°–50° C.) temperatures found in the carbon dioxide absorbant scrubber resulting from the normally exothermic reaction that occurs within the carbon dioxide scrubber during use in anesthesia and surgery. The process of the present invention has applicability with sevoflurane itself and also with the deuterated sevoflurane of our parent application. The novel process reported here is the discovery that the $CO_2$ scrubbing efficacy of sodalime is not materially diminished by externally cooling the sodalime during the $CO_2$ absorption process, despite markedly reducing or eliminating the breakdown of concomitantly applied sevoflurane. It is novel because no external cooling of sodalime has ever been done, for any reason, and it is not known that the $CO_2$ absorbing efficacy of sodalime remains high (clinically adequate), despite the virtual elimination of the undesirable reaction, namely the breakdown of sevoflurane or deuterated sevoflurane.

In vitro tests have demonstrated that deuterated sevoflurane, particularly with deuterium substitutions at the monofluoro substituted methyl group may be used in animals and as an inhalational anesthetic. One such deuterium substituted derivative found to be especially useful is fluorodideutero-methyl-1,1,1,3,3,3 -hexafluoro-2-propyl ether of which the following is a formula:

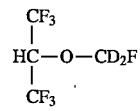

The compound retains all of the beneficial anesthetic qualities of sevoflurane as discussed earlier while at the same time markedly decreasing the exposure to fluoride. This result is surprising due to the fact that isomers of halogenated isopropyl ethers are largely unpredictable with respect to their anesthetic qualities. Further it has been demonstrated that deuterium substitution of ethers used as anesthetic compounds also quite unpredictable in their altered kinetics of metabolism.

U.S. Pat. No. 4,154 971 to Larsen et al. discloses mono-deuterated analogs of 1,1 difluoro 2,2-dihaloethyl difluoromethyl ethers. These are analogs of the anesthetics enflurane and isoflurane, not sevoflurane. Accordingly it was discovered that 1,1,2-trifluoro-2-chloro-2-deutero-ethyl difluoromethyl ether; 1,1-difluoro-2-deutero-2,2-dichloroethyl difluoromethyl ether; and 1,1,1 -trifluoro-2-bromo-2-deuteroethyl difluoromethyl ether all exhibited the characteristic of slower metabolism and thus slower defluorination. However, 1,1-difluoro-2,2-dichloro-2-deuteroethyl methyl ether exhibited properties of being more readily metabolized into inorganic fluoride than the undeuterated compound. This unpredictability of deuteration on fluoride ion release has similarly been encountered in other patented systems.

U.S. Pat. No. 4,153,636 similarly discloses deuterated analogs of the anesthetic methoxyflurane whrein 2,2-dichloro-1,1-difluro-1,methoxy-$d_3$-ethane and 2,2-dichloro-1,1-difluoro-1-methoxy-$d_3$-ethane were found to have decreased metabolism and again 1,1-difluoro-2,2-dichloro-2-deuteroethyl methyl ether was found to increase organic fluoride release.

The unpredictability of deuteration of anesthetics can also be demonstrated by the deuteration of halothane. Deuteration of halothane inhibits its metabolism to trifluoroacetic acid, but not its metabolism to release fluoride (Sipes I G, Gandolfi A J, Pohl L R, Krishna G, Brown Jr B R: Comparison of the biotransformation and hepatotoxicity of halothane and deuterated halothane. J. Pharmacol. Exp. Ther. 214: 716–720, 1980).

Thus it can be seen that the placement of deuterium atoms in the molecule is critical and highly species specific. $D_2$ sevoflurane with deuterium atoms at the monofluoro methyl group produces an unexpected unpredictable result of decreased rate of metabolism and decreased fluoride ion release while maintaining all the beneficial anesthetic properties of the compound.

According to the invention of our parent application, substitution of the hydrogens at the methyl group of sevoflurane with deuterium(D), a heavy isotope of hydrogen, alters the kinetics of metabolism of the compound. The compound retains its anesthetic qualities while being metabolized much more slowly thereby reducing production of inorganic fluoride. Substitution of the hydrogens at the methyl group of sevoflurane eliminates the concentration-dependent peak of fluoride release which occurs upon sevoflurane and enflurane metabolism in microsomes from isoniazid treated rats. Liver microsomes from isoniazid treated rats contain the same cytochrome P450 isozyme, P4502E1 which is present in humans and is inducible by ethanol, isoniazid and other compounds in humans.

D2-sevoflurane may be synthesized by modification of a method for synthesis of sevoflurane described in U.S. Pat. No. 3,683,092, the disclosure of which is incorporated herein by reference. The method is similar except, Dimethyl-$\underline{D}$6-sulfate, instead of dimethyl sulfate is reacted with 1,1,1,3,3,3-hexafluoroisopropranol to form trideuteromethyl-1,1,1,3,3,3-hexafluoro-2-propyl ether. The resulting trideuteromethyl-1,1,1,3,3,3-hexafluoro-2-propyl ether is then subsequently monofluorinated by reaction with bromine trifluoride.

D3-sevoflurane is synthesized by reacting D2-sevoflurane with NaOD in $D_2O$. The D2 sevoflurane is deuterated in the 2 propyl position to form fluoro-dideuteromethyl- 1,1,1,3,3,3-hexafluoro-2-deutero-2-propyl ether. All reactions are run with equimolar quantities of reactants preferred, although excesses of one or more of the variants may be used. No critical limits as to temperature or pressure exist, traditionally ambient conditions are used.

The end product, D2-sevoflurane or D3-sevoflurane may then be administered by the inhalation route to warm blooded, air breathing animals, in an effective anesthetizing amount. Generally the compound is administered in an amount of from about 1 percent to about 5 percent by volume in admixture with from 99 percent to about 95 percent by volume of oxygen or a gaseous mixture containing oxygen and/or other anesthetics (e.g. nitrous oxide).

In accordance with this improvement invention upon our parent application, degradation products are eliminated or minimized. The present invention is predicated upon the unpredictable finding that deliberate externally applied reduction in the temperature of sodalime during its exothermic reaction with carbon dioxide, to maintain the sodalime at ambient temperature or lower, eliminates production of the volatile degradation products of sevoflurane without significantly interfering with the ability of sodalime to scrub carbon dioxide.

In the typical exothermic $CO_2$ scrubbing used in an anesthesia circuit, the temperature of the sodalime increases to operating temperature from 44° C. to 50° C. In the process of the present invention, the sodalime is externally cooled and maintained at all times at room temperature or lower. Generally the temperature should be maintained within the range of from about 4° C. to about 30° C., preferably from about 4° C. to about 27° C., and most preferably from about 4° C. to about 20° C. Lowering of the temperature of the sodalime may be accomplished in several ways. One method is simply to use an ice water bath, wherein the canister is externally cooled in an ice water bath at all times. Another way is a refrigeration system associated with the typical sodalime canister, including using a heat exchanger, fans, etc. Other ways of conventional cooling to maintain a temperature in the sodalime within the herein expressed ranges will be apparent to those of ordinary skill in the art and need not be recited herein.

When temperatures are maintained within the range herein expressed, it only decreases sodalime carbon dioxide scrubbing efficiency by perhaps 20%. This however is an insignificant decrease since substantial excess sodalime is always used in an anesthesia machine.

The following examples are offered to further illustrate but not limit the process of this invention, which is only limited by the claims hereinafter set forth, and the appropriate application of the doctrine of equivalence to those claims, a doctrine upon which the applicants have relied for full protection of their defined invention.

EXAMPLE 1

To prepare trideuteromethyl-1,1,1,3,3,3 -hexafluoro-2-propyl ether, hexafluoroisoproponal (53.3 g) was added to 127 ml of 10% aqueous sodium hydroxide in a Pyrex flask. Dimethyl-D6-sulfate (40 g) was added proportion wise during a thirty-minute period at 5° C. while stirring. The reaction mixture was stirred for two hours at room temperature. Distillation of reaction mixture yielded 45 g of trideuteromethyl-1,1,1,3,3,3-hexafluoro-2-propyl ether.

D2-sevoflurane was obtained by placing 8 ml of dried trideuteromethyl-1,1,1,3,3,3-hexafluoro-2-propyl ether in a Pyrex flask. 3 ml of $BrF_3$ were slowly added over a two hour period while stirring. An exothermic reaction occurred, monofluorinating the ether compound. Following the reaction, water was cautiously added to destroy excess $BrF_3$ in the reaction mixture. The reaction mixture was successively washed with dilute sodium sulfate and water. Finally the washed mixture was dried over anhydrous sodium sulfate and yielded 3.1 ml D2-sevoflurane.

EXAMPLE 2

The formation of D2-sevoflurane and determination of its purity were evaluated by two methods of gas chromatography, and by GC-mass spectrometry using the electron impact (EI) and chemical ionization (CI) modes.

The synthesized product exhibited a retention time identical to that of sevoflurane on gas chromatography. D2-Sevoflurane chromatography on a carbowax column and using flame ionization detection, showed that the D2-sevoflurane was 99.86% pure. The contaminant at 7.0 minutes and constituting 0.032% of the sample was identified as hexafluoroisopropanol. Chromatography of the synthesized D2-sevoflurane sample on 10% CO-880 15% LB-550X indicates a purity of 99.9%. This column resolves methyl hexafluoroisopropyl ether or trideuteromethyl hexafluoropropyl ether (retention time of 2.2 minutes) from sevoflurane or D2-sevoflurane (3.3 minutes) and showed that the sample contained no trideuteromethyl-1,1,1,3,3,3-hexafluoro-2-propyl ether (or methyl hexafluoroisopropyl ether).

EXAMPLE 3

Mass spectral analysis of the synthesized D2-sevoflurane was performed on a Nermag R10-10C mass spectrometer in the electron impact and chemical ionization modes. The mass spectrometer was equipped with a DB Wax 30 m×0.2 mm×0.5 µm capillary column for sample introduction.

The electron impact mass spectra of sevoflurane and D2-sevoflurane were observed. The parent ion of either compound was not observed; however, the M-F and M-CF3 fragments occurred. Sevoflurane analysis yielded a M-F fragment with m/z of 181, whereas D2-sevoflurane produced a fragment of m/z 183—two atomic mass units greater. Also, sevoflurane generated a m/z fragment of 131 (M-CF3), whereas D2-sevoflurane showed the corresponding fragment at m/z 133—also two atomic mass units greater. The greater mass of 2 for these fragments confirms that the deuterated compound is fluoro-dideutero-methyl-1,1,1,3,3,3-hexafluoro-2-propyl ether, and the spectra showed that in the D2-sevoflurane sample no sevoflurane was detectable.

Mass spectra of sevoflurane and D2-sevoflurane in the chemical ionization mode showed the parent ion m/z (M+1) of 201 for sevoflurane and 203 for D2-sevoflurane. The parent ion of D2-sevoflurane was 2 atomic mass units greater than that of sevoflurane again confirming D2-sevoflurane.

EXAMPLE 4

Metabolism of D2-Sevoflurane

The metabolism of D2-sevoflurane is expected to liberate one fluoride ion for each molecule metabolized by cytochrome P450 since the metabolism of sevoflurane liberates fluoride and hexafluoroisopropanol. To determine the metabolism of D2-sevoflurane relative to sevoflurane and enflurane, these anesthetics were incubated with hepatic microsomes from untreated male Sprague-Dawley rats (200–230 g), or rats treated with isoniazid (80 mg/kg, i.p. for 5 days), or phenobarbital (0.2% in the drinking water for 4 days). Isoniazid induces the cytochrome P450 isozyme P450 2E1 which is thought to metabolize the volatile anesthetics, and phenobarbital induces several forms also shown to play a role in anesthetic metabolism in the rat.

Each incubation vial (6 ml plastic vial) contained 3 ml of 5 mg/ml microsomal protein in a 0.1M sodium phosphate buffer, pH 7.4. An NADPH generating system was added to cytochrome P450 activity, and the NADPH generating system was omitted from control incubations. Anesthetic was added in the quantities indicated and microsomes were incubated for 15 minutes at 37° C. Reactions were stopped by placing the vials on ice. Fluoride was assayed in the microsomal mixtures using fluoride ion-specific electrodes (Fisher Scientific) and a 720A Orion pH/ISE meter. Following incubation microsomes were mixed with an equal volume of TISABII buffer for fluoride analysis. Fluoride in each sample was determined from standard curves constructed using fluoride standards ($10^{-7}$ to $10^{-3}$M NaF) prepared from a commercially available standard solution ($10^{-1}$M NaF).

Comparison of the defluorination of D2-sevoflurane and sevoflurane in microsomes incubated with an excess of either anesthetic (1 µl anesthetic per incubation) shows that D2-sevoflurane is defluorinated much slower than sevoflurane in all microsomal preparations (table 1).

TABLE 1

COMPARATIVE DEFLUORINATION OF SEVO-
FLURANE AND $D_2$-SEVOFLURANE BY RAT LIVER
MICROSOMES*
nmol F$^-$/mg protein/30 min ± S.E.

| Animal Treatment | Sevoflurane | $D_2$-Sevoflurane |
|---|---|---|
| None | 1.94 ± 0.31 | 0.62 ± 0.60 (68)* |
| Isoniazid | 7.46 ± 0.83 | 1.55 ± 0.39 (79) |
| Phenobarbital | 1.18 ± 0.06 | 0.18 ± 0.03 (84) |

*Numbers in parentheses represent percent decline from sevoflurane values following correction for background (0.43). Values represent the mean and standard errors of triplicate determinations.

Figure 2:
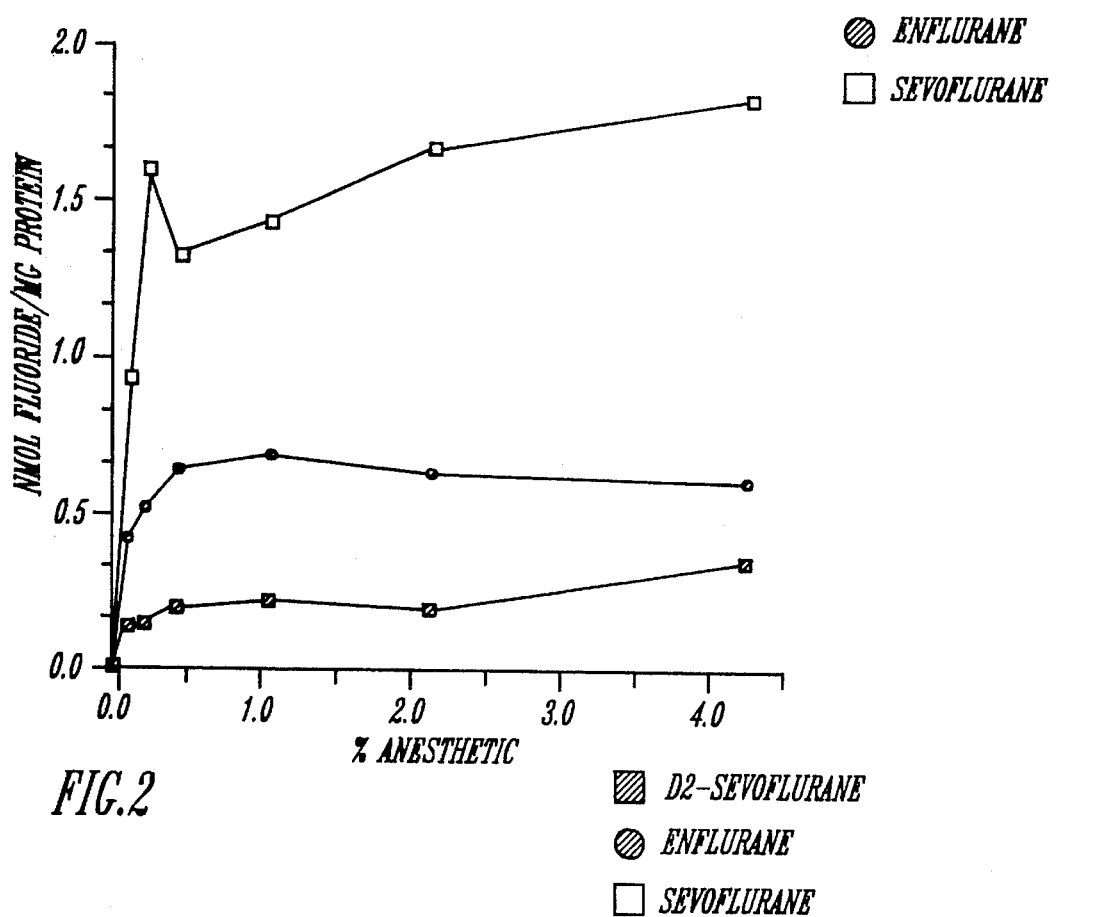
FIG. 2 is a graph depicting concentration dependent defluorination of deuterated sevoflurane, sevoflurane, and enflurane in hepatic microsomes from phenobarbital treated rats.

The degrees of inhibited metabolism are 68, 79 and 84% in microsomes from untreated, isoniazid and phenobarbital treated rats, respectively. The concentration-dependent defluorination of D2-sevoflurane, sevoflurane and enflurane, in microsomes from phenobarbital and isoniazid treated rats show that over a wide range of anesthetic concentrations D2-sevoflurane is defluorinated substantially slower than sevoflurane (70–86% less) or enflurane (FIGS. 1 and 2). In microsomes from isoniazid treated rats in which the metabolism of all anesthetics is the greatest due to the induction of P450 IIE1, there was an anesthetic concentration-dependent inhibition of metabolism by sevoflurane and enflurane, but not D2-sevoflurane (FIG. 1). These data suggests a substrate inhibition phenomenon. In microsomes from rats treated with phenobarbital this did not occur (FIG. 2).

EXAMPLE 5

In Vivo Metabolism of D2-Sevoflurane

Untreated rats or rats treated with isoniazid or phenobarbital were exposed to D2-sevoflurane, sevoflurane, or enflurane to determine the relative rates of fluoride production in vivo.

The animals were exposed in a 3.8 L plastic exposure chamber with an atmosphere of 100% oxygen. Male Sprague-Dawley rats (200–220 g, 4 per group) were placed in the chamber and the chamber was flushed with oxygen and sealed. Anesthetic was introduced into the chamber in liquid form via an injection port. Quantities were introduced to give initial concentrations of 3% anesthetic (enflurane, 464 µl; sevoflurane and D2-sevoflurane, 524 µl). The rats became anesthetized within 4–6 minutes after introduction of each anesthetic. Oxygen and carbon dioxide were monitored periodically during the exposure period with an Ohmeda 6000 multi-gas monitor.

Following a 30 minute exposure period, the chamber was flushed with 100% oxygen for 5 minutes and the animals rapidly awakened. The rats were immediately removed and injected i.p. with 80 mg/kg secobarbital. While anesthetized 3 to 4 ml of blood were withdrawn by cardiac puncture within 15 minutes of termination of anesthetic exposure (within 10 minutes of removal from the chamber). Plasma was prepared and fluoride analyzed as described above.

Figure 3:
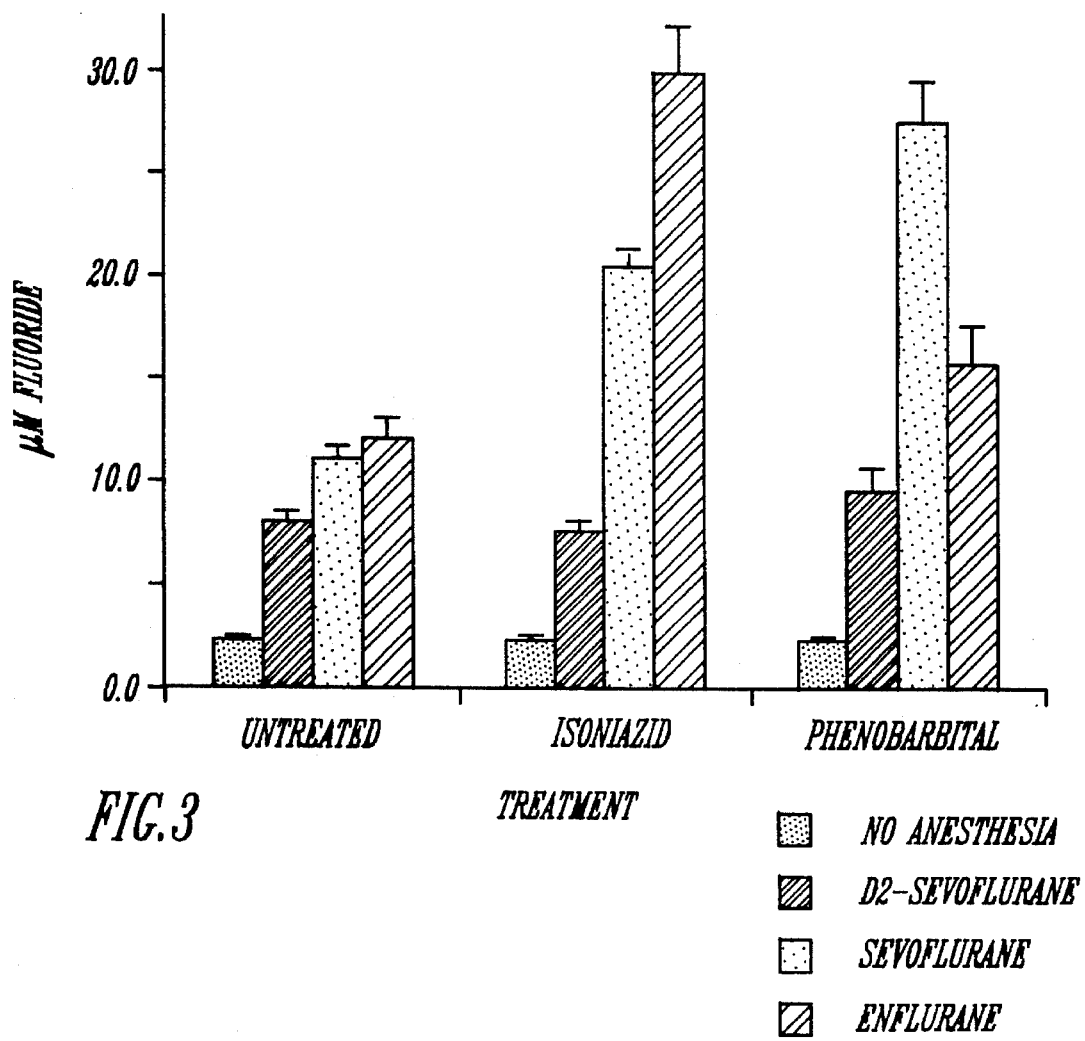
FIG. 3 is a bar graph depicting Plasma fluoride levels in rats anesthetized for 30 minutes with deuterated sevoflurane, sevoflurane, and enflurane.

Exposure to D2-sevoflurane resulted in lower plasma fluoride than exposure to either enflurane or sevoflurane (FIG. 3). As compared to the liberation of fluoride from sevoflurane, D2-sevoflurane liberated 61% less in isoniazid treated rats, 66% less in phenobarbital treated animals, and 34% less in untreated rats. D2-sevoflurane also liberated less fluoride than enflurane in vivo. In untreated, and isoniazid and phenobarbital treated rats, the plasma from D2-sevoflurane exposed rats contained 40, 80, and 45%, respectively, less fluoride than enflurane anesthetized animals.

EXAMPLE 6

An anesthesia circuit containing fresh sodalime (1.5 kg) was set up with an anesthesia machine (Foregger F 500). Sevoflurane at an initial concentration of 2.7% (a relatively high anesthetic concentration) was added to the circuit and 100% oxygen was used as the makeup gas. The gases were recirculated at a total circuit flow rate of 1.5 liters per minute (a relatively low clinical total flow rate) in a closed system with a respirator. Carbon dioxide was added to the circuit at a constant rate of 200 ml per minute. This set up the conditions for "worst case" breakdown of sevoflurane by sodalime.

Experiments were conducted at exothermic temperature versus with the sodalime canister immersed in an ice bath. When the experiments were conducted at exothermic temperatures, the temperature in the core of the sodalime stabilized at between 44° C. and 47° C. after about one hour. Degradation products from the breakdown of sevoflurane were detected at about 1.5 hours after the circuit was started. Products were continually detected for the remainder of the experiments (up to eight hours) by gas chromatography. However, when the canister was immersed in the ice bath, the core temperature of the sodalime canister equilibrated at between 22° C. and 27° C. when stabilized. It never increased above this range. Using the same chromatography analysis, no degradation products were detected in this system, which was also run for up to eight hours. Carbon dioxide levels on the respiratory side of the circuit were completely scrubbed and were no different between sodalime in ice or at ambient temperature.

Incubations of sevoflurane with sodalime in static systems also showed this same effect. At 22° C. some degradation products including "Compound A" were detected; however, at 45° C. substantial degradation products, including "Compound A", were produced. Similar experiments were run with deuterated sevoflurane and results were essentially the same.

From these experiments, it was concluded that maintaining the sodalime temperature in the range of 4° C. to 27° C. reduced the production of volatile degradation by-products of sevoflurane or deuterated sevoflurane to virtually insignificant levels.

It can therefore be seen that the invention accomplished at least all of its stated objectives.

What is claimed is:

1. A method of inducing anesthesia in mammals using volatile anesthetics, said method comprising the concurrent, continuous and repetitive steps of:

administering by inhalation to a mammal effective amounts of a volatile anesthetic including sevoflurane or deuterated sevoflurane until a desired depth of anesthesia is achieved;

providing a chemical carbon dioxide scrubber; and collecting exhaled gases including exhaled anesthetic from a mammal and passing such through said chemical carbon dioxide scrubber containing basic carbon dioxide absorbent chemicals and thereafter returning at least part of such gases from said chemical carbon dioxide scrubber including the anesthetic back to a mammal via the admisistering step; and reducing the formation of toxic compounds from volatile anesthetic in the chemical scrubber and the delivery thereof to a mammal by externally maintaining the scrubber and the chemicals thereof at temperatures less than about 30 degrees C. for countering exothermic heating due to the gas passage through the scubber.

2. The method of claim 1 further comprising: externally maintaining chemicals contained by the carbon dioxide scrubber and the gases discharged therefrom at temperatures between about 4 degrees C. and about 30 degrees C.

3. The method of claim 1 further comprising: externally maintaining chemicals contained by the carbon dioxide scrubber and the gases discharged therefrom at temperatures between about 4 degrees C. and about 27 degrees C.

4. The method of claim 1 further comprising: externally maintaining chemicals contained by the carbon dioxide scrubber and the gases discharged therefrom at temperatures between about 4 degrees C. and about 20 degrees C.

5. The method of claim 1 further comprising: providing an ice bath; and maintaining the carbon dioxide scrubber and the chemicals thereof and thus the gases discharged therefrom at said temperatures by using an ice bath.

6. The method of claim 1 further comprising: providing a heat exchanger device; and maintaining the carbon dioxide scrubber and the chemicals thereof and thus the gases discharged therefrom at said temperatures by using a heat exchanger device.

* * * * *